(12) United States Patent
Faraone (10) Patent No.: US 8,859,560 B2
(45) Date of Patent: Oct. 14, 2014

(54) TREATING ATTENTION DEFICIT HYPERACTIVITY DISORDER WITH NHE INHIBITORS

(71) Applicant: The Research Foundation of State University of New York, Syracuse, NY (US)

(72) Inventor: Stephen V. Faraone, Sanibel, FL (US)

(73) Assignee: The Research Foundation of State University of New York, Syracuse, NY (US)

( * ) Notice: Subject to any disclaimer, the term of this patent is extended or adjusted under 35 U.S.C. 154(b) by 0 days.

(21) Appl. No.: 13/768,989

(22) Filed: Feb. 15, 2013

(65) Prior Publication Data

US 2013/0217707 A1    Aug. 22, 2013

Related U.S. Application Data

(60) Provisional application No. 61/601,900, filed on Feb. 22, 2012.

(51) Int. Cl.
| | | |
|---|---|---|
| *A61K 31/4965* | (2006.01) | |
| *A61K 31/437* | (2006.01) | |
| *A61K 31/66* | (2006.01) | |
| *A61K 31/49* | (2006.01) | |
| *G01N 33/94* | (2006.01) | |
| *A61K 31/166* | (2006.01) | |
| *A61K 31/165* | (2006.01) | |

(52) U.S. Cl.
CPC ............ *A61K 31/4965* (2013.01); *G01N 33/94* (2013.01); *A61K 31/166* (2013.01); *G01N 2800/305* (2013.01); *A61K 31/49* (2013.01); *A61K 31/165* (2013.01); *A61K 31/437* (2013.01)
USPC ....... 514/255.06; 514/618; 514/305; 514/292

(58) Field of Classification Search
USPC .............................. 514/255.06, 618, 305, 292
See application file for complete search history.

(56) References Cited

PUBLICATIONS

Yanli (SLC9A9E mutations, gene expression and protein-protein interactions in rat models of attention-deficit/hyperactivity disorder, Am Journal Medical Genet B Neurophsychiatric Genet. Dec. 2011: 156(7), pp. 835-843, renumbered 1-15).*

Masereel et al., "An Overview of Inhibitors of Na+/H+ Exchanger," European Journal of Medicinal Chemistry 38:547-554 (2003).
Zhang-James et al., "Differential Expression of SLC9A9 and Interacting Molecules in the Hippocampus of Rat Models for Attention Deficit/Hyperactivity Disorder," Dev. Neurosci. 34(2-3):218-227 (2012).
Lasky-Su et al., "Genome-Wide Association Scan of Quantitative Traits for Attention Deficit Hyperactivity Disorder Identifies Novel Associations and Confirms Candidate Gene Associations," American Journal of Medical Genetics Part B (Neuropsychiatric Genetics) 147B:1345-1354 (2008).
Lasky-Su et al., "Genome-Wide Association Scan of the Time to Onset of Attention Deficit Hyperactivity Disorder," American Journal of Medical Genetics Part B (Neuropsychiatric Genetics) 147B:1355-1358 (2008).
Mick et al., "Family-Based Genome-Wide Association Scan of Attention-Deficit/Hyperactivity Disorder," Journal of the American Academy of Child & Adolescent Psychiatry, 49(9):898-905.e3 (2010).
Markunas et al., "Genetic Variants in SLC9A9 are Associated with Measures of Attention-Deficit/Hyperactivity Disorder Symptoms in Families," Psychiatr. Genet. 20(2):73-81 (2010).
Grisel et al., "Quantitative Trail Loci Affecting Methamphetamine Responses in BXD Recombinant Inbred Mouse Strains," The Journal of Neuroscience 17(2):745-754 (1997).
Moisan et al., "Further Dissection of a Genomic Locus Associated with Behavioral Activity in the Wistar-Kyoto Hyperactive Rat, an Animal Model of Hyperkinesis," Molecular Psychiatry 8:348-352 (2003).
De Silva et al., "Disruption of a Novel Member of a Sodium/Hydrogen Exchanger Family and DOCK3 is Associated with an Attention Deficit Hyperactivity Disorder-Like Phenotype," J. Med. Genet. 40:733-740 (2003).
Mathis et al., "Genetic Analysis of Anxiety-Related Behaviors and Responses to Benzodiazepine-Related Drugs in AXB and BXA Recombinant Inbred Mouse Strains," Behavior Genetics 25(6):557-568 (1995).
Miner et al., "Chromosomal Mapping of the Psychomotor Stimulant Effects of Cocaine in BXD Recombinant Inbred Mice," Psychopharmacology 122(3):209-214 (1995).

* cited by examiner

*Primary Examiner* — San-Ming Hui
*Assistant Examiner* — Kathrien Cruz
(74) *Attorney, Agent, or Firm* — LeClairRyan, a Professional Corporation

(57) ABSTRACT

The present invention relates to a method of treating attention deficit hyperactivity disorder in a subject. This method includes selecting a subject with attention deficit hyperactivity disorder and administering to the selected subject a sodium/hydrogen exchanger inhibitor under conditions effective to treat the subject for attention deficit hyperactivity disorder. Methods of identifying compounds suitable to treat attention deficit hyperactivity disorder are also disclosed.

4 Claims, 4 Drawing Sheets

Figure 3: Multidimensional Scaling of Molecular Descriptor Similarity among Drugs

TREATING ATTENTION DEFICIT HYPERACTIVITY DISORDER WITH NHE INHIBITORS

This application claims the benefit of U.S. Provisional Patent Application Ser. No. 61/601,900, filed Feb. 22, 2012, which is hereby incorporated by reference in its entirety.

This invention was made with government support under grant number R01MH66877 awarded by National Institute of Mental Health. The U.S. Government has certain rights in this invention.

FIELD OF THE INVENTION

The present invention relates to treating attention deficit hyperactivity disorder (ADHD) with sodium/hydrogen exchange (NHE) inhibitors.

BACKGROUND OF THE INVENTION

Attention deficit hyperactivity disorder (ADHD) is a common childhood disorder associated with school failure, psychiatric comorbidity, and disability. Most cases persist into adulthood, causing occupational failure, criminality, traffic accidents, increased medical health care utilization, and substance use disorders. In adulthood, the cost of ADHD to society is estimated between $77.5 and $115.9 billion annually. Biederman, et. al., "The Effects of Attention-deficit Hyperactivity Disorder on Employment and Household Income," *Medscape Ge. Med.* 8(3): 12 (2006). These costs, which are considerable in both human and financial terms, are magnified by the painfully long duration of the disorder and the low efficacy of current treatments.

ADHD is a highly-heritable disorder. Faraone, et. al., "Molecular Genetics of Attention Deficit Hyperactivity Disorder," *Psychiat. Clin. N. Am.* 33(1): 159-80 (2010) and Gizer, et. al., "Candidate Gene Studies of ADHD: A Meta-analytic Review," *Hum. Genet.* 126(1): 51-90 (2009). Genetic, brain imaging, and animal model studies have implicated numerous candidate genes in its etiology. Faraone, et. al., "Molecular Genetics of Attention Deficit Hyperactivity Disorder," *Psychiat. Clin. N. Am.* 33(1): 159-80 (2010) and Gizer, et. al., "Candidate Gene Studies of ADHD: A Meta-analytic Review," *Hum. Genet.* 126(1): 51-90 (2009). In addition, some environmental exposures such as premature birth, low birth weight, and maternal smoking in pregnancy contribute to the etiology of ADHD. Genetic studies also suggest that rare genetic variants can cause ADHD in some patients.

Although medications for ADHD currently exist, some are scheduled substances. In addition, their efficacy is limited, and they are associated with adverse effects that limit their use.

The present invention is directed to overcoming these deficiencies in the art.

SUMMARY OF THE INVENTION

The present invention relates to a method of treating attention deficit hyperactivity disorder in a subject. This method includes selecting a subject with attention deficit hyperactivity disorder and administering to the selected subject a sodium/hydrogen exchanger (NHE) inhibitor under conditions effective to treat the subject for attention deficit hyperactivity disorder.

Another aspect of the present invention relates to a method of identifying a therapeutic for treating attention deficit hyperactivity disorder. This method includes providing a sodium/hydrogen exchanger, providing a collection of candidate compounds, contacting the sodium/hydrogen exchanger with members of the collection of compounds, and identifying candidate compounds which bind to the sodium/hydrogen exchanger as being potentially useful for treating attention deficit hyperactivity disorder.

A further aspect of the present invention relates to a method of identifying a therapeutic for treating attention deficit hyperactivity disorder. This method comprises providing a collection of candidate compounds, analyzing whether the candidate compounds will bind to the sodium/hydrogen exchanger, and identifying, as a result of said analyzing, the candidate compounds which will bind to the sodium/hydrogen exchanger as being potentially useful for treating attention deficit hyperactivity disorder.

It is expected that the clinical use of sodium/hydrogen exchange inhibitors for treating ADHD will improve the lives of many ADHD patients and their families. Although several pharmacologic options for ADHD exist, a substantial minority are considered nonresponders due to insufficient symptom reduction or inability to tolerate existing medications (Wender, P. H., "Pharmacotherapy of Attention-Deficit/Hyperactivity Disorder in Adults," *J Clin Psychiatry* 59(7):76-9 (1998) and Wilens et al., "A Review of the Pharmacotherapy of Adults with Attention-Deficit/Hyperactivity Disorder," *Journal of Attention Disorders* 5:189-202 (2002), which is hereby incorporated by reference in their entirety). And many "responders" only experience a 50% or less reduction of the core symptoms of ADHD (Biederman et al., "Influence of Gender on Attention Deficit Hyperactivity Disorder in Children Referred to a Psychiatric Clinic," *Am J Psychiatry* 159: 36-42 (2002), which is hereby incorporated by reference in its entirety). Moreover, currently available treatments do not markedly improve deficits in executive functioning or emotional self-regulation (Faraone et al., "Atomoxetine and Executive Functioning in Adult Attention Deficit Hyperactivity Disorder," *Journal of Child and Adolescent Psychopharmacology* 15:664-670 (2005); Reimherr et al., "Emotional Dysregulation as a Core Feature of Adult ADHD: Its Relationship with Clinical Variables and Treatment Response in Two Methylphenidate Trials," *Journal of ADHD and Related Disorders* 1:53-64 (2010); Reimherr et al., "A Double-Blind, Placebo-Controlled, Crossover Study of Osmotic Release Oral System Methylphenidate in Adults with ADHD with Assessment of Oppositional and Emotional Dimensions of the Disorder," *J Clin Psychiatry* 68:93-101 (2007); Rhodes et al., "Acute Neuropsychological Effects of Methylphenidate in Stimulant Drug-Naive Boys with ADHD II—Broader Executive and Non-Executive Domains," *J Child Psychol Psychiatry* 47:1184-94 (2006); Schweitzer et al., "Effect of Methylphenidate on Executive Functioning in Adults with Attention-Deficit/Hyperactivity Disorder: Normalization of Behavior But Not Related Brain Activity," *Biol Psychiatry* 56:597-606 (2004); and Tannock et al., "Effects of Methylphenidate on Inhibitory Control in Hyperactive Children," *Journal of Abnormal Child Psychology* 17:473-491 (1989), which are hereby incorporated by reference in their entirety). Also, the treatment of ADHD, in accordance with the present invention, would provide a new alternative to non-stimulants. Because current non-stimulants are less effective than stimulants (Faraone et al., "A Comparison of the Efficacy of Medications for Adult Attention-Deficit/Hyperactivity Disorder Using Meta-Analysis of Effect Sizes," *J Clin Psychiatry* 71:754-63 (2010), which is hereby incorporated by reference in its entirety), it is possible that sodium/hydrogen exchange inhibitors will provide a more efficacious non-stimulant alternative. The potential impact of sodium/hydrogen exchange inhibitors is broad, because: a) ADHD is a common disorder affecting 6% of children (Faraone et al., "The Worldwide Prevalence of ADHD: Is it an American Condition?," *World Psychiatry* 2:104-113 (2003), which is hereby incorporated by reference in its entirety); b) in the majority of cases, the disorder persists into adulthood (Biederman et al., "Attention Deficit Hyperactivity Disorder," *Lancet* 366:237-248 (2005), which is hereby incorporated by reference in its entirety) and c) the disorder is associated with serious impairments including traffic accidents (Biederman et al., "Attention Deficit Hyperactivity Disorder," *Lancet* 366:237-248 (2005), which is hereby incorporated by reference in its entirety), increased health care utilization (Biederman et al., "Attention Deficit Hyperactivity Disorder," *Lancet* 366:237-248 (2005), which is hereby incorporated by reference in its entirety), substance abuse (Biederman et al., "Attention Deficit Hyperactivity Disorder," *Lancet* 366:237-248 (2005), which is hereby incorporated by reference in its entirety), unemployment (Biederman et al., "Attention Deficit Hyperactivity Disorder," *Lancet* 366:237-248 (2005), which is hereby incorporated by reference in its entirety), divorce (Biederman et al., "Attention Deficit Hyperactivity Disorder," *Lancet* 366:237-248 (2005), which is hereby incorporated by reference in its entirety), and AIDs risk behaviors (Barkley et al., "ADHD in Adults: What the Science Says," Guilford Press: New York, N.Y. (2008), which is hereby incorporated by reference in its entirety). The economic impact of ADHD is between $77.5 and $115.9 billion each year (Biederman et al., "The Effects of Attention-Deficit Hyperactivity Disorder on Employment and House Hold Income," *Medscape General Medicine* 8:12 (2006), which is hereby incorporated by reference in its entirety). Although medications for ADHD are effective in controlling symptoms for many patients, they do not "cure" the disorder. As we have shown in our longitudinal study of ADHD children (Biederman et al., "Predictors of Persistence and Remission of ADHD: Results From a Four-Year Prospective Follow-Up Study of ADHD Children," *Journal of the American Academy of Child and Adolescent Psychiatry* 35:343-351 (1996), which is hereby incorporated by reference in its entirety), even those receiving treatment are at risk for adverse outcomes.

DETAILED DESCRIPTION OF THE INVENTION

The present invention relates to a method of treating attention deficit hyperactivity disorder in a subject. This method includes selecting a subject with attention deficit hyperactivity disorder and administering to the selected subject a sodium/hydrogen exchanger (NHE) inhibitor under conditions effective to treat the subject for attention deficit hyperactivity disorder.

Suitable NHE inhibitors include amiloride, dimethyl amiloride, cariporide, methyl isobutyl amiloride, hydrochlorothiazide, eplerenone, benzamil, cimetidine, harmaline, benzoylguanidine, Hoechst type inhibitor compounds, spironolactone, triamterene, metolazone, bumetanide, furo-semide, torsemide, chlorothiazide, chlorthalidone, indapamide, methyclothiazide, ethacrynate, dihydrothiaphenanthrene carbonylguanidine, aminosterol compounds, acyl guanidines, heterocyclic NHE inhibitors, monocyclic, bicyclic and tricyclic guanidine derivatives, substituted anthranilic acids, quinolone-4-carbonylguanidine derivatives, 5-aryl-4-(4-(5-methyl-1H-imidazol-4-yl)piperidin-1-yl)pyrimidine analogs, bicyclic acylguanidines, 2-methyl-5-(methylsulfonyl)benzoyl)guanidines, arylcyclopropanecarboxyl guanidines, zoniporide, aminoimidazoles, 5-aryl-4-(4-(5-methyl-1H-imidazol-4-yl)piperidin-1-yl)pyrimidine analogs, 4-substituted (benzo[b]thiophene-2-carbonyl) guanidines, substituted indan-1-ylideneaminoguanidine derivatives, 2-aryl-5-methylimidazol-4-ylcarbonyl) guanidines, 2-aryl-5-methyloxazol-4-ylcarbonyl) guanidines, substituted-(5-arylfuran-2-ylcarbonyl) guanidines, 5-arylfuran-2-ylcarbonyl)guanidines, benzimidazol-2-yl, benzimidazol-2-ylthiomethyl benzoylguanidine, amiloride hydrochloride, cimetidine hydrochloride, aldactone, dyrenium, zaroxolyn, chlorothiazide sodium, and thalitone. See also the inhibitors disclosed in Masereel et al., "An Overview of Inhibitors of Na+/H+ Exchanger," *Euro. J. Med. Chem.* 38:547-54 (2003), which is hereby incorporated by reference in its entirety.

Of the sodium hydrogen exchanger inhibitors, sodium/hydrogen exchange-9 inhibitors are preferred in carrying out the present invention.

Administration of the compound of the present invention can be, without limitation, carried out systematically. Exemplary methods of administering the compounds of the present invention include, without limitation, parental, oral, subcutaneous, intravenous, intramuscular, extraperitoneal, intranasal instillation, by inhalation, or by application to mucuous membrane administration.

While it may be possible for compounds of the present invention to be administered as the raw chemical, it will often be preferable to present them as part of a pharmaceutical composition. Accordingly, another aspect of the present invention is a pharmaceutical composition containing a therapeutically effective amount of a compound of the present invention, or a pharmaceutically acceptable salt or solvate thereof, and a pharmaceutically acceptable carrier or diluent. The carrier must be "acceptable" in the sense of being compatible with the other ingredients of the formulation and not deleterious to the recipient thereof. Furthermore, when reference is made in an independent claim to a compound or a pharmaceutically acceptable salt thereof, it will be understood that claims which depend from that independent claim which refer to such a compound also include pharmaceutically acceptable salts of the compound, even if explicit reference is not made to the salts.

The amount of active ingredient that may be combined with the carrier materials to produce a single dosage form will vary depending upon the host treated and the particular mode of administration. For example, a formulation intended for the oral administration of humans may vary from about 5 to about 95% of the total composition. Dosage unit forms will generally contain between from about 1 mg to about 500 mg of active ingredient.

Any pharmaceutically acceptable liquid carrier suitable for preparing solutions, suspensions, emulsions, syrups and elixirs may be employed in the composition of the invention. Compounds of the present invention may be dissolved or suspended in a pharmaceutically acceptable liquid carrier such as water, an organic solvent, or a pharmaceutically acceptable oil or fat, or a mixture thereof. The liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration, the carrier may also be an oily ester such as ethyl oleate or isopropyl myristate.

Pharmaceutically acceptable salts include, but are not limited to, amine salts, such as but not limited to N,N'-dibenzyl-ethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine, and tris (hydroxymethyl) aminomethane; alkali metal salts (e.g., lithium, potassium, and sodium), alkali earth metal salts (e.g., barium, calcium, and magnesium), transition metal salts (e.g., zinc), and other metal salts (e.g., sodium hydrogen phosphate and disodium phosphate), salts of mineral acids (e.g., hydrochlorides and sulfates), and salts of organic acids (e.g., acetates, lactates, malates, tartrates, citrates, ascorbates, succinates, butyrates, valerates and fumarates). Pharmaceutically acceptable esters include, but are not limited to, alkyl, alkenyl, alkynyl, aryl, heteroaryl, cycloalkyl and heterocyclyl esters of acidic groups, including, but not limited to, carboxylic acids, phosphoric acids, phosphinic acids, sulfonic acids, sulfinic acids, and boronic acids. Pharmaceutical acceptable enol ethers include, but are not limited to, derivatives of formula C=C(OR) where R is hydrogen, alkyl, alkenyl, alkynyl, aryl, heteroaryl, cycloalkyl, or heterocyclyl. Pharmaceutically acceptable enol esters include, but are not limited to, derivatives of formula C=C(OC(O)R) where R is hydrogen, alkyl, alkenyl, alkynyl, aryl, heteroaryl, cycloalkyl, or heterocyclyl. Pharmaceutical acceptable solvates and hydrates are complexes of a compound with one or more solvent or water molecules, or 1 to about 100, or 1 to about 10, or one to about 2, 3 or 4, solvent or water molecules.

It will be understood, however, that the specific dose level for any particular patient will depend upon a variety of factors, including the activity of the specific compound employed, the age, body weight, general health, sex, diet time of administration, route of administration, rate of excretion, drug combination and the severity of the particular disease undergoing therapy.

All methods comprise administering to the patient in need of such treatment an effective amount of one or more compounds of the present invention.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The compounds of the present invention can be administered alone or as an active ingredient of a formulation. Thus, the present invention also includes pharmaceutical compositions of one or more compounds of the present invention containing, for example, one or more pharmaceutically acceptable carriers. The compounds of the present invention can be administered in a form where the active ingredient is substantially pure.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition), which are hereby incorporated by reference in their entirety.

Solid carriers suitable for use in the composition of the invention include one or more substances which may also act as flavoring agents, lubricants, solubilizers, suspending agents, fillers, glidants, compression aides, binders, tablet-disintegrating agents, or encapsulating materials. In powders, the carrier may be a finely divided solid which is in admixture with a finely divided compound of the present invention. In tablets, compounds of the present invention may be mixed with a carrier having the necessary compression properties in suitable proportions and compacted in the shape and size desired. Said powders and tablets may contain up to 99% by weight of the compound of the present invention. Solid carriers suitable for use in the composition of the present invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes, and ion exchange resins.

Formulations suitable for oral administration may be presented as discrete units such as capsules, cachets, or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary, or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active, or dispersing agent. Molded tablets may be made by molding in a suitable machine a mixture of the powdered compound moistened with an inert liquid diluent. The tablets may optionally be coated or scored and may be formulated so as to provide sustained, delayed, or controlled release of the active ingredient therein. The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or non-aqueous techniques, "Pharmaceutically acceptable carrier" also encompasses controlled release means.

Pharmaceutical compositions may also optionally include other therapeutic ingredients, anti-caking agents, preservatives, sweetening agents, colorants, flavors, desiccants, plasticizers, dyes, and the like. Any such optional ingredient must be compatible with the compounds of the present invention to insure the stability of the formulation. The composition may contain other additives as needed, including for example lactose, glucose, fructose, galactose, trehalose, sucrose, maltose, raffinose, maltitol, melezitose, stachyose, lactitol, palatinite, starch, xylitol, mannitol, myoinositol, and the like, and hydrates thereof, and amino acids, for example alanine, glycine and betaine, and peptides and proteins, for example albumen.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents.

Another aspect of the present invention relates to a method of identifying a therapeutic for treating attention deficit hyperactivity disorder. This method includes providing a sodium/hydrogen exchanger, providing a collection of candidate compounds, contacting the sodium/hydrogen exchanger with members of the collection of compounds, and identifying candidate compounds which bind to the sodium/hydrogen exchanger as being potentially useful for treating attention deficit hyperactivity disorder. Preferably, this method is carried out with sodium/hydrogen exchanger-9.

A further aspect of the present invention relates to a method of identifying a therapeutic for treating attention deficit hyperactivity disorder. This method comprises providing a collection of candidate compounds, analyzing whether the candidate compounds will bind to the sodium/hydrogen exchanger, and identifying, as a result of said analyzing, the candidate compounds which will bind to the sodium/hydrogen exchanger as being potentially useful for treating attention deficit hyperactivity disorder. Preferably, this method is carried out with sodium/hydrogen exchanger-9.

The methods according to the present invention involve evaluating contact between the candidate compounds and the model to determine which of the one or more candidate compounds have an ability to bind to and/or fit in a model of the present invention. The evaluation of the candidate compounds, which may be a part of a library of compounds, is a central task in the drug-design process. The evaluation of candidate compounds is a means to assess the binding properties of the candidate compounds and ascertain the most promising candidates. There are many ways known in the art which can be used to evaluate the candidate compounds and are described (Kitchen et al., "Docking and Scoring in Virtual Screening for Drug Discovery: Methods and Applications," *Nature Reviews. Drug Discovery* 3: 935-49 (2004); Lengauer et al., "Computational Methods for Biomolecular Docking," *Curr. Opin. Struct. Biol.* 6: 402-6 (1996); Wei et al., "Testing a Flexible-receptor Docking Algorithm in a Model Binding Site," *J. Mol. Biol.* 337: 1161-82 (2004); Meng et al., "Automated Docking with Grid-based Energy Evaluation," *Journal of Computational Chemistry* 13: 505-524 (2004); Morris et al., "Automated Docking Using a Lamarckian Genetic Algorithm and an Empirical Binding Free Energy Function," *Journal of Computational Chemistry* 19: 1639-1662 (1998); Schneider et al., "Computer based de novo Design of Druglike Molecules," *Nature Reviews* 4:649-663, which are hereby incorporated by reference in their entirety). Scoring functions can rank the candidate compounds based on their binding to the target and also provide a guide during the design process through the search space.

Many software tools are available for molecular modeling. For example, MODELLER is a popular software tool for producing homology models using methodology derived from NMR spectroscopy data processing. SwissModel provides an automated web server for basic homology modeling. I-TASSER is a server for protein structure prediction according to the recent CASP experiments (CASP7 and CASP8). Common software tools for protein threading are HHpred/HHsearch, Robetta, and Phyre. RAPTOR is a protein threading software that is based on integer programming. The basic algorithm for threading is described in Bowie et al., "A Method to Identify Protein Sequences that Fold into a Known Three-dimensional Structure," *Science* 253: 164-170 (1991), which is hereby incorporated by reference in its entirety, and is fairly straightforward to implement. Abalone is a Molecular Dynamics program for folding simulations with explicit or implicit water models.

Typical suites of software include CERIUS$^2$ (Accelrys, San Diego, Calif.), SYBYL (Tripos Inc., St. Louis, Mo.), AMBER (University of California, San Francisco), HYPERCHEM (Hypercube Inc., Gainesville, Fla.), INSIGHT II (Accelrys, San Diego, Calif.), CATALYST (Accelrys, San Diego, Calif.), CHEMSITE (ChemSW, Fairfield, Calif.), QUANTA (Accelrys, San Diego, Calif.). These packages implement many different algorithms that may be used according to the present invention (e.g. CHARMM molecular mechanics (Brooks et al., "CHARMM: A Program for Macromolecular Energy, Minimization, and Dynamics Calculations," *J. Comp. Chem.* 4, 187-217 (1983), which is hereby incorporated by reference in its entirety).

Compounds can be evaluated for their ability to interact with the target by using their respective atomic co-ordinates in automated docking algorithms. An automated docking algorithm is one which permits the prediction of interactions of a number of compounds with a molecule having a given atomic structure.

Suitable docking algorithms include: DOCK (Kuntz et al., "A Geometric Approach to Macromolecule-ligand Interactions," *J Mol Biol.* 161(2):269-88 (1982), which is hereby incorporated by reference in its entirety), AUTODOCK (Goodsell et al. *Proteins: Structure, Function and Genetics* 8:195-202 (1990), which is hereby incorporated by reference in its entirety), MOE-DOCK (Chemical Computing Group, Montreal Canada) or FLEXX (BioSolveIT GmbH, Sankt Augustine, Germany). Docking algorithms can also be used to verify interactions with ligands designed de novo.

EXAMPLES

Example 1

Evidence for new etiologic pathways is combined with bioinformatics data to assess the possibility that existing drugs might be repositioning for treating ADHD. This approach was used to determine if prior human and animal data implicating the sodium/hydrogen exchanger 9 gene (SLC9A9) in ADHD correctly implicate NHE inhibitors as potential treatments for ADHD. The potential for repositioning by assessing the similarity of drug-protein binding profiles between NHE inhibitors and drugs known to treat ADHD was determined using the Drug Repositioning and Adverse Reaction via Chemical-Protein Interactome (DRAR-CPI) server. The results of this evaluation show that NHE9 has a high degree of amino acid similarity with NHE inhibitor sensitive NHEs in the region of the NHE inhibitor recognition site that has been defined for NHE1. High correlations in drug-protein binding profiles were found among most ADHD drugs. The drug-protein binding profiles of some NHE inhibitors were highly correlated with ADHD drugs whereas the profiles for a control set of nonsteroidal anti-inflammatory drugs were not. The results suggest that further experimental work should be done to determine if some NHE inhibitors might be suitable for treating ADHD.

Genetic, brain imaging, and animal model studies of ADHD have suggested numerous common DNA variants to be associated with the disorder (Faraone et al., "Molecular Genetics of Attention Deficit Hyperactivity Disorder," *Psychiatr Clin North Am* 33:159-180 (2010) and Gizer et al., "Candidate Gene Studies of ADHD: A Meta-analytic Review," *Hum Genet.* 126:51-90 (2009), which are hereby incorporated by reference in their entirety, and studies of copy number variation suggest that rare DNA variants cause ADHD in some patients. These DNA variants likely combine with environmental exposures such as premature birth, low birth weight, and maternal smoking in pregnancy to create a complex etiology for ADHD.

It has been the hope of molecular genetic studies that the discovery of new etiologically relevant biological pathways would provide new targets for ADHD treatment. New treatments for ADHD are needed for two reasons. About 25 percent of ADHD patients do not respond well to currently available therapies (Biederman et al., "Systematic Chart Review of the Pharmacologic Treatment of Comorbid Attention Deficit Hyperactivity Disorder in Youth With Bipolar Disorder," *Journal of Child and Adolescent Psychopharmacology* 9:247-256 (1999), which is hereby incorporated by reference in its entirety). Although medications for ADHD are effective in controlling symptoms for many patients, they do not "cure" the disorder; even those receiving treatment are at risk for adverse outcomes (Biederman et al. "Predictors of Persistence and Remission of ADHD: Results from a Four-year Prospective Follow-up Study of ADHD Children," *Journal of the American Academy of Child and Adolescent Psychiatry* 35:343-351 (1996), which is hereby incorporated by reference in its entirety). Currently available treatments improve outcome, but they leave patients with much residual disability. They do not markedly improve the executive dysfunction or deficits in emotional self-regulation seen in many ADHD patients. These treatments also have adverse effects, including small delays in growth (Faraone et al., "Effect of Stimulants on Height and Weight: A Review of the Literature," *J Am Acad Child Adolesc Psychiatry* 47:994-1009 (2008), which is hereby incorporated by reference in its entirety).

Ideally, new treatment targets would derive from functional, mechanistic studies of variants unequivocally implicated in the etiology of a disorder. Such data are not currently available for ADHD. Another approach is to combine evidence for new etiologic pathways with bioinformatics data to assess the possibility that existing drugs might be repurposed, or repositioned for treating ADHD. Here, the hypothesis that treatments based on a novel ADHD target would emerge from a bioinformatics analysis of drug repositioning is tested.

The target of interest is sodium/hydrogen exchanger isoform 9 (SLC9A9). This gene was first implicated in ADHD by a report of an extended family in which ADHD co-segregated with a pericentric inversion of Chromosome 3 that disrupted both DOCK3 and SLC9A9(de Silva et al., "Disruption of a Novel Member of a Sodium/Hydrogen Exchanger Family and DOCK3 is Associated With an Attention Deficit Hyperactivity Disorder-like Phenotype," *J Med Genet.* 40:733-740 (2003), which is hereby incorporated by reference in its entirety). In a study of the WKHA rat model of ADHD, a single genome-wide significant locus (Act QTL) on Chromosome 8 that contains SLC9A9 showed significant linkage to the ADHD trait of hyperactivity (Moisan et al., "Further Dissection of a Genomic Locus Associated with Behavioral Activity in the Wistar-Kyoto Hyperactive Rat, an Animal Model of Hyperkinesis," *Mol Psychiatry* 8:348-352 (2003), which is hereby incorporated by reference in its entirety). The Act QTL locus is homologous to the region of human Chromosome 3 where the pericentric inversion disrupting SLC9A9 segregated with ADHD (de Silva et al., "Disruption of a Novel Member of a Sodium/Hydrogen Exchanger Family and DOCK3 is Associated With an Attention Deficit Hyperactivity Disorder-like Phenotype," *J Med Genet.* 40:733-740 (2003), which is hereby incorporated by reference in its entirety). Moreover, the homologous region in mouse Chromosome 9 that contains SLC9A9 contains an activity-related QTL (Grisel et al., "Quantitative Trait Loci Affecting Methamphetamine Responses in BXD Recombinant Inbred Mouse Strains," *J Neurosci* 17:745-754 (1997); Mathis et al., "Genetic Analysis of Anxiety-related Behaviors and Responses to Benzodiazepine-related Drugs in AXB and BXA Recombinant Inbred Mouse Strains," *Behav Genet.* 25:557-568 (1995); and Miner et al., "Chromosomal Mapping of the Psychomotor Stimulant Effects of Cocaine in BXD Recombinant Inbred Mice," *Psychopharmacology (Berl)* 122:209-214 (1995), which are hereby incorporated by reference in their entirety).

Single nucleotide polymorphisms (SNPs) in SLC9A9 were identified among the most significant findings in an analysis of 51 candidate genes from the International Multi-site ADHD Genetics (IMAGE) project (Brookes et al., "The Analysis of 51 Genes in DSM-IV Combined Type Attention Deficit Hyperactivity Disorder: Association Signals in DRD4, DAT1 and 16 Other Genes," *Mol Psychiatry* (2006), which is hereby incorporated by reference in its entirety). In the IMAGE genome-wide association study (GWAS) of ADHD symptoms, SLC9A9 achieved one of the lowest P values (~10-5 (Lasky-Su et al., "Genome-wide Association Scan of Quantitative Traits for Attention Deficit Hyperactivity Disorder Identifies Novel Associations and Confirms Candidate Gene Associations," *Am J Med Genet B Neuropsychiatr Genet.* 147B:1345-1354 (2008), which is hereby incorporated by reference in its entirety). Although SLC9A9 was also associated with ADHD in a subsequent association study by another group (Markunas et al., "Genetic Variants in SLC9A9 are Associated with Measures of Attention-deficit/Hyperactivity Disorder Symptoms in Families," *Psychiatr Genet.* 20:73-81 (2010), which is hereby incorporated by reference in its entirety), it has not achieved genomewide significance (Neale et al., "Meta-analysis of Genome-wide Association Studies of Attention-deficit/Hyperactivity Disorder," *J Am Acad Child Adolesc Psychiatry* 49:884-897 (2010), which is hereby incorporated by reference in its entirety). In another GWAS study, SLC9A9 was nominally associated with nicotine dependence (Uhl et al., "Molecular Genetics of Nicotine Dependence and Abstinence: Whole Genome Association Using 520,000 SNPs," *BMC Genet.* 8:10 (2007), which is hereby incorporated by reference in its entirety), which is also associated with ADHD (Biederman et al., "Parsing the Associations Between Prenatal Exposure to Nicotine and Offspring Psychopathology in a Nonreferred Sample," *J Adolesc Health* 45:142-148 (2009) and Monuteaux et al., "A Randomized, Placebo-controlled Clinical Trial of Bupropion for the Prevention of Smoking in Children and Adolescents with Attention-deficit/Hyperactivity Disorder," *J Clin Psychiatry* 68:1094-1101 (2007), which are hereby incorporated by reference in their entirety).

The spontaneously hypertensive (SHR) rat obtained from Charles River, Germany (SHR/NCrl) is a well-validated animal model of the ADHD-Combined subtype (ADHD-C), with the Wistar-Kyoto strain obtained from Harlan, UK (WKY/NHsd) being its most appropriate control (Sagvolden T., "Behavioral Validation of the Spontaneously Hypertensive Rat (SHR) as an Animal Model of Attention-deficit/Hyperactivity Disorder (AD/HD)," Neurosci Biobehav Rev 24:31-39 (2000) and Sagvolden et al., "The Spontaneously Hypertensive Rat Model of ADHD—the Importance of Selecting the Appropriate Reference Strain," Neuropharmacology 57:619-626 (2009), which are hereby incorporated by reference in their entirety). A new rat model for the inattentive subtype of ADHD (WKY/NCrl, obtained from Charles River, Germany) (Sagvolden et al., "Behavioral and Genetic Evidence for a Novel Animal Model of Attention-Deficit/Hyperactivity Disorder Predominantly Inattentive Subtype," Behav Brain Funct 4:56 (2008), which is hereby incorporated by reference in its entirety). This rat, which shows impaired sustained attention, but normal activity level and impulsiveness, is genetically divergent from the common reference WKY strain (WKY/NHsd). It was found that there was increased dopamine transporter (DAT) expression and activity in the nigrostriatal system of the WKY/NCrl rat as well as SHR/NCrl rat (Roessner et al., "Methylphenidate Normalizes Elevated Dopamine Transporter Densities in an Animal Model of the Attention-deficit/Hyperactivity Disorder Combined Type, but not to the Same Extent in one of the Attention-deficit/Hyperactivity Disorder Inattentive Type," Neuroscience 167:1183-1191 (2010), which is hereby incorporated by reference in its entirety), supporting the possibility that DAT dysregulation, which has been implicated in human ADHD (Spencer et al., "Further Evidence of Dopamine Transporter Dysregulation in ADHD: A Controlled PET Imaging Study Using Altropane," Biol Psychiatry 62:1059-1061 (2007) and Yang et al., "A Meta-analysis of Association Studies Between the 10-repeat Allele of a VNTR Polymorphism in the 3'-UTR of Dopamine Transporter Gene and Attention Deficit Hyperactivity Disorder," Am J Med Genet B Neuropsychiatr Genet. 144B:541-550 (2007), which are hereby incorporated by reference in their entirety) is abnormal in these animal models of the disorder.

It was subsequently assessed mRNA expression in the medial prefrontal cortex, dorsal striatum, and hippocampus of these animal models. Prefrontal cortex and dorsal striatum) had been implicated in ADHD by a meta-analysis of structural imaging studies in humans (Valera et al., "Meta-analysis of Structural Imaging Findings in Attention-deficit/Hyperactivity Disorder," Biological psychiatry 61:1361-1369 (2007), which is hereby incorporated by reference in its entirety). Abnormal hippocampal structure had also been observed in ADHD patients (Plessen et al., "Hippocampus and Amygdala Morphology in Attention-deficit/Hyperactivity Disorder," Arch Gen Psychiatry 63:795-807 (2006), which is hereby incorporated by reference in its entirety) and in SHR rats (Amenta et al., "Vascular and Neuronal Hypertensive Brain Damage: Protective Effect of Treatment with Nicardipine," J Hypertens Suppl 14:S29-35 (1996), which is hereby incorporated by reference in its entirety), and hippocampus plays an essential role in cognitive functions impaired in ADHD such as learning and memory, attention (Goldstein et al., "Role of the Anterior Cingulate and Medial Orbitofrontal Cortex in Processing Drug Cues in Cocaine Addiction," Neuroscience 144:1153-1159 (2007), which is hereby incorporated by reference in its entirety), and decision-making (Ernst et al., "Neural Substrates of Decision Making in Adults With Attention Deficit Hyperactivity Disorder," American Journal of Psychiatry 160:1061-1070 (2003), which is hereby incorporated by reference in its entirety). It was found that there was increased SLC9A9 expression in hippocampus (for adult WKY/NCrl rats) and prefrontal cortex (for adult SHR/NCrl) rats. The differences with control WKY/NHsd rats were statistically significant whether or not SLC9A9 expression was corrected for synaptophysin (SYP) expression, which is correlated with neuronal proliferation, fiber outgrowth and the formation of synapses (Grabs et al., "Differential Expression of SYNAPTOphysin and Synaptoporin During Pre- and Postnatal Development of the Rat Hippocampal Network," Eur J Neurosci 6:1765-1771 (1994), which is hereby incorporated by reference in its entirety). SHR/NCrl rats showed no DNA sequence variations in the SLC9A9 coding region, but it was found five novel SNPs in the inattentive WKY/NCrl rats, including two nonsynonymous mutations in highly-conserved regions (V512G and K534R). These mutations were always found together.

The two non-synonymous mutations are located in the intracellular C-terminal juxtamembrane region of SLC9A9, where regulatory proteins normally bind. This region shares some degree of homology with other members of the NHE protein family, whose binding partners are well-characterized (the terminology NHE9 is used to refer to the protein coded by the SLC9A9 gene and likewise for other family members). We examined the effects of the mutations on the interaction of SLC9A9 protein with two predicted protein partners: calcineurin homologous protein (CHP) and receptor for activated protein kinase C (RACK1). The mutations significantly increased the amount of CHP precipitated with SLC9A9 by almost two-fold but had no effect on RACK1.

It is not yet known what the mechanism is by which NHE9 overactivation leads to excess dopamine transporter activity and ADHD symptoms. One possible mechanism underlying the role of SLC9A9 in neural activity is its role as a local signaling scaffold protein. Mammalian sodium-hydrogen exchangers have a long intracellular C-terminal, which recruits various signaling molecules, and may promote the assembly of local signaling complexes and coordinate divergent signaling pathways (Baumgartner et al., "Na(+)/H(+) Exchanger NHE1 as Plasma Membrane Scaffold in the Assembly of Signaling Complexes," Am J Physiol Cell Physiol 287:C844-85 (2004), which is hereby incorporated by reference in its entirety). It has been shown that the NHE9 C-terminal interacts with the signaling molecules CHP and RACK1. These molecules are involved in the calcium signaling and protein phosphorylation signaling pathways which mediate synaptic transmission and plasticity. In addition, by regulating endosomal pH, NHE9 regulates the intracellular trafficking and recycling of receptors and transporters (Park et al., "Recycling Endosomes Supply AMPA Receptors for LTP," Science 305:1972-1975 (2004) and Park et al., "Plasticity-induced Growth of Dendritic Spines by Exocytic Trafficking from Recycling Endosomes," Neuron 52:817-830 (2006), which are hereby incorporated by reference in their entirety), including the dopamine transporter, a target for ADHD medications (Melikian et al., "Membrane Trafficking Regulates the Activity of the Human Dopamine Transporter," J Neurosci 19:7699-7710 (1999), which is hereby incorporated by reference in its entirety).

Because very little is known about the structure and biology of NHE9, no studies have yet been conducted to determine if it is targeted by existing drugs. In contrast, a large literature describes molecules that inhibit NHE1-NHE7, with most of this work focused on NHE1-NHE5 (Karmazyn M, Avkiran M, Fliegel L editors The Sodium-Hydrogen Exchanger: From Molecule to its Role in Disease. Norwell, Mass.: Kluwer Academic Publisher (2003) and Masereel et al., "An Overview of Inhibitors of Na(+)/H(+) Exchanger," *Eur J Med Chem* 38:547-554 (2003), which are hereby incorporated by reference in their entirety). NHE inhibitors are used as diuretics, anti-hypertensive agents, and for the prevention of cardiac or neural ischemia (Karmazyn M, Avkiran M, Fliegel L editors *The Sodium-Hydrogen Exchanger: From Molecule to its Role in Disease*. Norwell, Mass.: Kluwer Academic Publisher (2003) and Masereel et al., "An Overview of Inhibitors of Na(+)/H(+) Exchanger," *Eur J Med Chem* 38:547-554 (2003), which are hereby incorporated by reference in their entirety). The potential for these drugs to inhibit NHE9 is unclear, because studies of NHE inhibitors have focused on plasma membrane NHEs (NHE1-NHE5) and not organelle specific NHEs (NHE6-NHE9) and the two types of NHEs show some structural divergence in their amino acid sequences (Nakamura et al., "Four Na+/H+ Exchanger Isoforms are Distributed to Golgi and Post-Golgi Compartments and are Involved in Organelle pH Regulation," *J Biol Chem* 280:1561-1572 (2005), which is hereby incorporated by reference in its entirety). Although the overall amino acid similarity between the two classes of NHE inhibitors is low (23-27%), the membrane regions are more highly conserved, with about 50% amino acid identity between classes (Nakamura et al., "Four Na+/H+ Exchanger Isoforms are Distributed to Golgi and Post-Golgi Compartments and are Involved in Organelle pH Regulation," *J Biol Chem* 280: 1561-1572 (2005), which is hereby incorporated by reference in its entirety). Of particular relevance to ADHD, clonidine is a modest inhibitor of plasma membrane NHEs (Karmazyn M, Avkiran M, Fliegel L editors *The Sodium-Hydrogen Exchanger: From Molecule to its Role in Disease*. Norwell, Mass.: Kluwer Academic Publisher (2003) and Masereel et al., "An Overview of Inhibitors of Na(+)/H(+) Exchanger," *Eur J Med Chem* 38:547-554 (2003), which are hereby incorporated by reference in their entirety), and is also a moderately efficacious drug for ADHD (Jain et al., "Clonidine Extended-release Tablets for Pediatric Patients With Attention-deficit/Hyperactivity Disorder," *J Am Acad Child Adolesc Psychiatry* 50:171-179 (2011), which is hereby incorporated by reference in its entirety).

In summary, five pieces of evidence suggest that medications which inhibit sodium-hydrogen exchange proteins could treat ADHD symptoms: 1) SLC9A9 is associated with ADHD in humans; 2) SLC9A9 mRNA expression is increased in ADHD-relevant brain regions in two rat models of ADHD; 3) one rat model of ADHD has mutations in SLC9A9; 4) the rat mutations are associated with greater than normal binding of CHP, which would be expected to increase the activity of NHE9 and 5) clonidine is a modest NHE inhibitor and a moderately effective ADHD medication.

The present work sought to test two hypotheses derived from the idea that current NHE inhibitors might be useful for the treatment of ADHD via inhibition of NHE9. First, it was hypothesized that there is substantial similarity of the amino acid sequence in the binding region for NHE inhibitors between NHE9 and NHEs known to be inhibited by NHE inhibitors. Such a finding would suggest that these drugs would inhibit NHE9.

Second, if NHE9 inhibition is useful for the treatment of ADHD, it is possible that, in addition to clonidine, other ADHD medications might have a dual mechanism of effect much as clonidine inhibits sodium-hydrogen exchange and also agonizes the adrenergic alpha-2A receptor. To assess this possibility, it is hypothesized that an in silico approach from drug repositioning methodology would find a correspondence between the drug-protein binding profile of ADHD medications and those of NHE inhibitors. Although, theoretically, in silico methods could assess the binding affinity of these medications with NHE9, that is not possible because the three dimensional structure of NHE9 is unknown. In contrast, it is feasible to computationally estimate the binding affinity of each drug with a panel of proteins of known structure. As shown by (Luo et al., "DRAR-CPI: A Server for Identifying Drug Repositioning Potential and Adverse Drug Reactions Via the Chemical-Protein Interactome," *Nucleic Acids Res:* 1-7 (2011); Yang et al., "Harvesting Candidate Genes Responsible for Serious Adverse Drug Reactions from a Chemical-protein Interactome," *PLoS Comput Biol* 5:e1000441 (2009); and Yang et al., "SePreSA: A Server for the Prediction of Populations Susceptible to Serious Adverse Drug Reactions Implementing the Methodology of a Chemical-Protein Interactome," *Nucleic Acids Res* 37:W406-412 (2009), which are hereby incorporated by reference in their entirety), using such a panel, similar protein binding affinities between drugs can be used to predict similar binding affinities with proteins not included in the panel. The rationale for this approach is the idea that two drugs having a similar pattern of binding to other proteins should have similar biological and therapeutic effects.

It is hypothesized that drug-protein binding profiles would be similar between ADHD medications and NHE inhibitors and that these similarities would be associated with the molecular properties of the drugs.

Example 2

To compare the amino acid sequences of NHE9 with other NHEs, human NHE sequences were multiply aligned using ClustalW and the BLOSUM62 alignment score matrix. A cluster plot of NHE amino acid sequence similarity was created in Jalview 2.6.2. Although Nakamura et al., "Four Na+/H+ Exchanger Isoforms are Distributed to Golgi and Post-Golgi Compartments and are Involved in Organelle pH Regulation," *J Biol Chem* 280:1561-1572 (2005), which is hereby incorporated by reference in its entirety, had previously presented the amino acid similarities of NHE proteins, applicant's focus was on the NHE inhibitor recognition region which was shown experimentally to involve residues within the fourth and ninth membrane spanning helices (these are bounded by amino acids 150 and 400) (Khadilkar et al., "Identification of Sites in the Second Exomembrane Loop and Ninth Transmembrane Helix of the Mammalian Na+/H+ Exchanger Important for Drug Recognition and Cation Translocation," *J Biol Chem* 276:43792-43800 (2001), which is hereby incorporated by reference in its entirety).

To assess the correspondence between the drug-protein binding profile of ADHD medications and those of NHE inhibitors, the drug repositioning methodology of Luo et al., "DRAR-CPI: A Server for Identifying Drug Repositioning Potential and Adverse Drug Reactions Via the Chemical-protein Interactome," *Nucleic Acids Res:* 1-7 (2011); Yang et al., "Harvesting Candidate Genes Responsible for Serious Adverse Drug Reactions from a Chemical-Protein Interactome," *PLoS Comput Biol* 5:e1000441 (2009); and Yang et al., "SePreSA: A Server for the Prediction of Populations Susceptible to Serious Adverse Drug Reactions Implementing the Methodology of a Chemical-Protein Interactome," *Nucleic Acids Res* 37:W406-412 (2009), which are hereby incorporated by reference in their entirety, was used. This approach uses a collection of 392 structural models of targetable human proteins from UniProt and 582 active forms of drug molecules from DrugBank having known treatment indications. These targets were required to have known, targetable sites with binding pockets that were screened according to several criteria to assure the presence of a suitable binding pocket (for details, see Yang et al., "Harvesting Candidate Genes Responsible for Serious Adverse Drug Reactions from a Chemical-protein Interactome," *PLoS Comput Biol* 5:e1000441 (2009) and Yang et al., "SePreSA: A Server for the Prediction of Populations Susceptible to Serious Adverse Drug Reactions Implementing the Methodology of a Chemical-protein Interactome," *Nucleic Acids Res* 37:W406-412 (2009), which are hereby incorporated by reference in their entirety). This database is known as the Drug Repositioning and Adverse Reaction via Chemical-Protein Interactome (DRAR-CPI).

To assess the similarity of the drugs of interest with the drug-protein binding profile of the drugs in DRAR-CPI, a structural model of the drug molecule was submitted to the DRAR-CPI server. The structure of each drug, in SMILES format, was retrieved from PubChem. These were then input to CORINA to generate minimal energy conformations. The CORINA files were translated into .ml2 files by VEGA ZZ. These structural models were hybridized in silico with each protein target in the DRAR-CPI database using DOCK (Ewing et al., "DOCK 4.0: Search Strategies for Automated Molecular Docking of Flexible Molecule Databases," *J Comput Aided Mol Des* 15:411-428 (2001), which is hereby incorporated by reference in its entirety). The ability of the molecule to dock with the target is quantified as a z-score such that z-scores less than −0.5 indicate that the molecule tends to bind with the protein.

Five drugs approved by the US Food and Drug Administration for the treatment of ADHD (methylphenidate, amphetamine, guanfacine, atomoxetine and clonidine) were used. Six NHE inhibitors chosen due to prior knowledge about their pattern of selectivity for NHE subtypes were examined (Masereel et al., "An Overview of Inhibitors of Na(+)/H(+) Exchanger," *Eur J Med Chem* 38:547-554 (2003), which is hereby incorporated by reference in its entirety): amilioride and benzamil have limited NHE subtype selectivity; cariporide selectively inhibits NHE1; 53226 selectively inhibits NHE3; quinine selectively inhibits NHE7; harmaline selectively inhibits NHE5. To control for the possibility that DRAR-CPI might produce spurious correlations, the association of ADHD drugs with five nonsteroidal anti-inflammatory drugs (NSAIDs), for which there was no prior reason to believe would be associated with ADHD drugs (i.e. naproxen, aspirin, ibuprofen, celecoxib and rofecoxib) were tested.

The statistical analyses used DRAR-CPI to compute z-scores indicating the degree to which each drug is predicted to bind to the 389 protein targets in the DRAR-CPI database. These z-scores between each ADHD drug and a) other ADHD drugs; b) the NHE inhibitors and c) the NSAIDs drugs used as controls were correlated. A positive correlation means that two drugs share similar patterns of drug-protein binding across all of the targets in the DRAR-CPI database. To visualize similarity of drug-protein binding predictions among drugs, classical multidimensional scaling using Euclidean distance as the similarity metric, the stress criterion as the loss function, and principal normalization as the normalization method were used. These analyses were accomplished with STATA (StataCorp 2007).

E-DRAGON was used to compute molecular descriptors in four categories: 48 constitutional descriptors, 261 three dimensional descriptors, 121 topological descriptors, and 22 molecular property descriptors. To assess the similarity of drugs as regards these molecular descriptors, multidimensional scaling as described above was used. A seemingly unrelated regression analysis was utilized to assess the association of drug subsets with drug-protein binding and with molecular descriptors. This regression method provides joint estimates from several regression models when the error terms of the models are correlated.

Example 3

Figure 1:
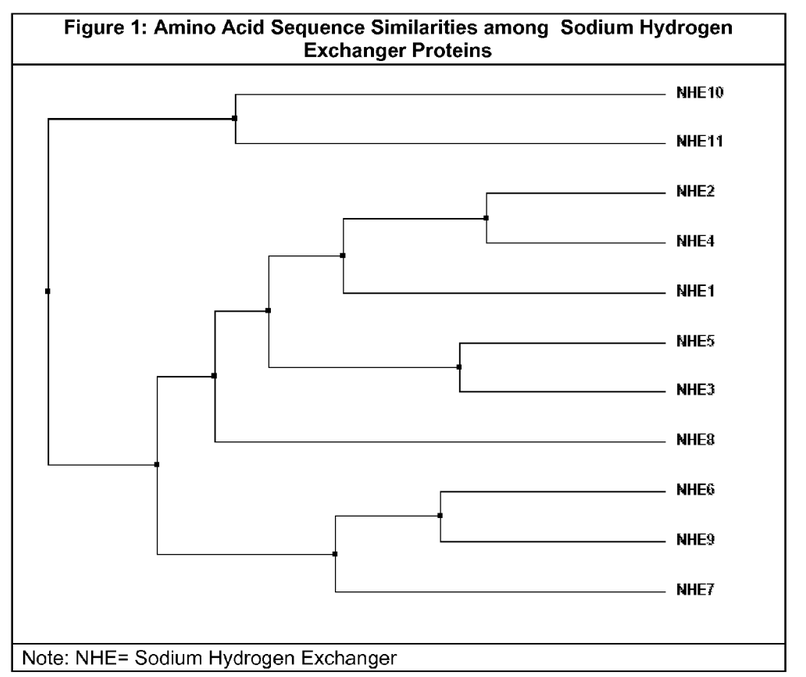
FIG. 1 discloses the amino acid sequence similarities among sodium hydrogen exchanger proteins.

As FIG. 1 shows, in the predicted transmembrane region, NHE9 is most similar to NHE6 and NHE7. There is one large cluster comprising NHE1-5 and NHE8 and a third cluster with NHE10 and NHE11. The percent of identical or similar positions between NHE9 and NHEs shown experimentally to be sensitive to NHE inhibitors are NHE1: 68%, NHE2: 72.4%; NHE3: 65.6%; NHE4: 72.8% and NHE5: 64.4%.

Table 1 shows the results of the analyses correlating protein binding affinity z-scores between drugs.

TABLE 1

Significant Drug-Protein Binding Correlations between ADHD Drugs and Other Drugs

| | MPH | AMPH | ATX | GUAN | CLON |
|---|---|---|---|---|---|
| Attention Deficit Hyperactivity Disorder Drugs | | | | | |
| methylphenidate | 1.00 | 0.73 | 0.78 | 0.74 | . |
| dextroamphetamine | 0.73 | 1.00 | 0.75 | 0.84 | . |
| atomoxetine | 0.78 | 0.75 | 1.00 | 0.81 | . |
| guanfacine | 0.74 | 0.84 | 0.81 | 1.00 | . |
| clonidine | . | . | . | . | . |
| Sodium/Hydrogen Exchange Inhibitors | | | | | |
| cariporide | 0.65 | 0.65 | 0.70 | 0.71 | . |
| amiloride | 0.70 | 0.86 | 0.79 | 0.88 | 0.21 |
| S3226 | 0.61 | 0.60 | 0.72 | 0.72 | . |
| benzamil | 0.68 | 0.71 | 0.75 | 0.72 | 0.23 |
| quinine | . | −0.31 | . | −0.21 | . |
| harmaline | . | −0.21 | . | . | 0.55 |
| Nonsteroidal Anti-inflammatory Drugs | | | | | |
| naproxen | −0.59 | −0.49 | −0.56 | −0.50 | . |
| aspirin | −0.53 | −0.37 | −0.53 | −0.45 | . |
| ibuprofen | −0.56 | −0.44 | −0.56 | −0.53 | . |
| celecoxib | . | . | . | . | . |
| rofecoxib | . | −0.27 | . | −0.20 | . |

Note:
MPH = methylphenidate; AMPH = amphetamine; ATX = atomoxetine; GUAN = guanfacine; CLON = clonidine; Only correlations significant at the Bonferroni corrected level of p < 0.0004 are presented.

With the exception of clonidine, all ADHD drugs were highly and significantly correlated with other ADHD drugs. Thus, the DRAR-CPI drug-protein database recovers most of the expected associations among ADHD drugs.

For the NHE inhibitors amiloride, cariporide, S3226, and benzamil, drug-binding profiles were significantly positively correlated with methylphenidate, amphetamine, atomoxetine, and guanfacine. Benzamil and amiloride were also positively correlated with clonidine. Quinine showed modest negative association with two ADHD drugs. Harmaline was negatively correlated with amphetamine and positively correlated with clonidine. No NSAID drug was positively correlated with any ADHD drug. Several significant, albeit, modest negative correlations were observed.

Figure 2:
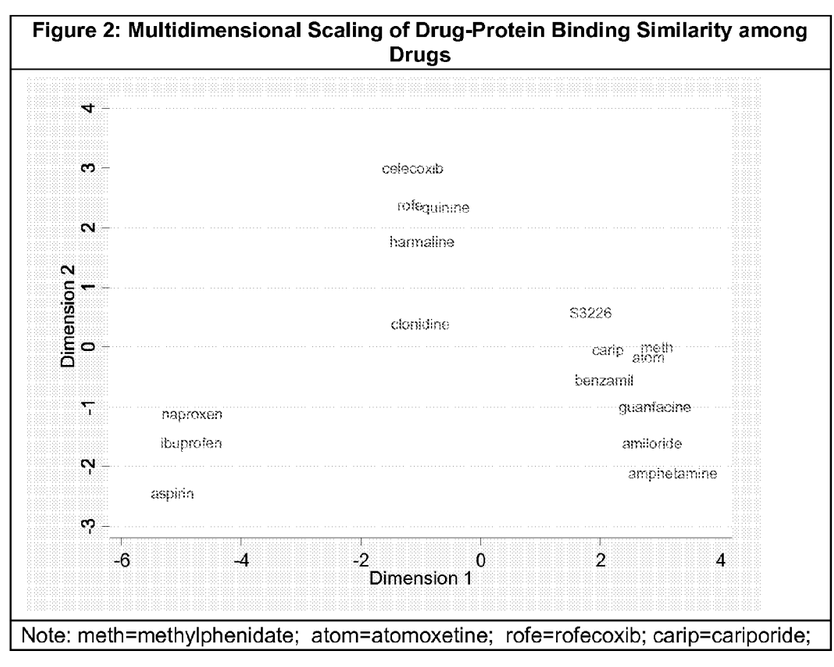
FIG. 2 shows the multi-dimensional scaling of drug-protein binding similarity among drugs.

Multidimensional scaling was used to visualize the similarity of drug-protein binding among the drugs in Table 1. Two dimensions accounted for 95.8% of the variance. The mean correlation between observed drug differences in drug-protein binding and the Euclidean distances of the two dimensional solution was 0.97, indicating an excellent fit of the model. FIG. 2 plots the two dimensional solution. The lower right hand corner of this figure shows a cluster of drugs comprising all ADHD drugs (except clonidine) and four NHE inhibitors: amiloride, benzamil, S2226, and cariporide. The small cluster on the lower left contains three NSAIDs. The upper-middle cluster contains two NSAIDs and two NHE inhibitors (harmaline and quinine) Clonidine did not cluster with other drugs.

Figure 3:
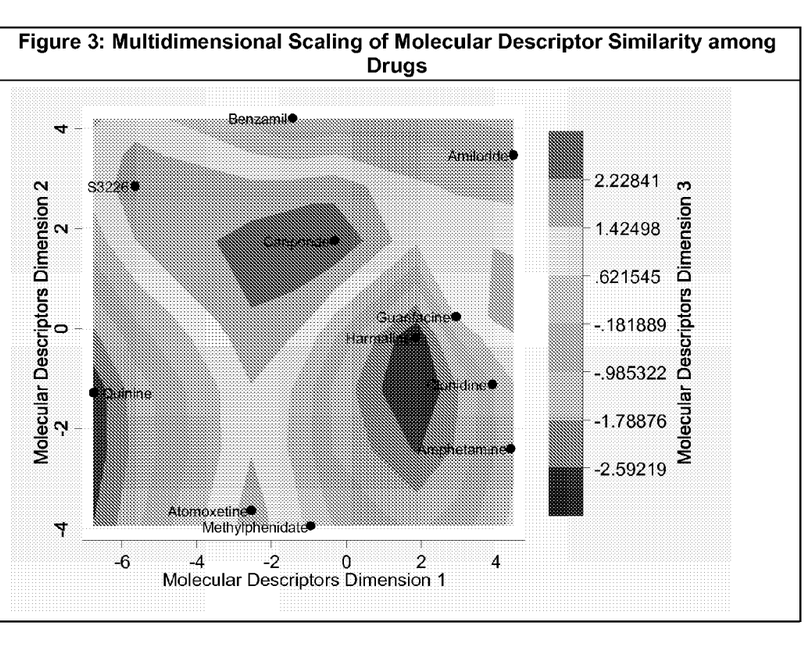
FIG. 3 discloses the multi-dimensional scaling of molecular descriptor similarity among drugs.

Because the analyses of drug-protein interaction indicated that two of the NHE inhibitors (quinine and harmaline) and one ADHD drug (clonidine) did not associate with other ADHD drugs, applicant sought to determine if that could be accounted for by the properties of these molecules. A multi-dimensional scaling of the molecular descriptors of the ADHD and NHE inhibitor drugs, extracted three dimensions accounting for 86% of the variance. The mean correlation between observed drug differences in molecular descriptors and the Euclidean distances of the two dimensional solution was 0.96, indicating an excellent fit of the model. The three dimensional solution is given in FIG. 3.

Figure 4:
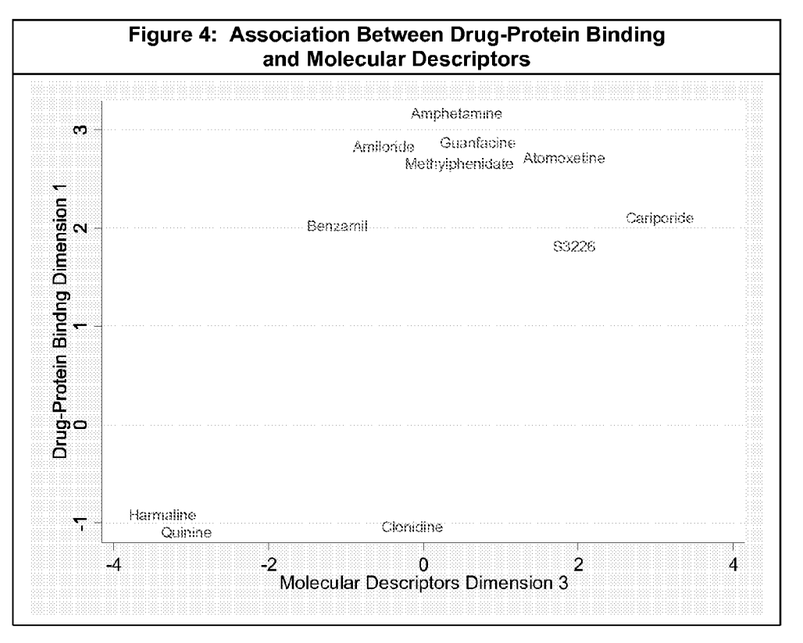
FIG. 4 shows the association between drug-protein binding and molecular descriptors.

Regression analysis showed that clonidine, quinine, and harmaline differed significantly from the other drugs on the third molecular features dimension ($z=3.4$, $p=0.001$) but not the first two molecular feature dimensions ($p$'s$>0.5$). Regression analyses also found that drug-protein binding dimension one was significantly associated with molecular descriptor dimension three ($z=2.98$, $p=0.003$). FIG. 4 illustrates this association and highlights the separation of harmaline, quinine, and clonidine from the other drugs. Drug-protein binding dimension two was associated with molecular descriptor dimensions one ($z=3.46$, $p=0.001$) and three ($z=2.68$, $p=0.007$).

Example 4

The above results provide two sources of information that support the hypothesis that NHE inhibitors act on NHE9 and have anti-ADHD efficacy. First, NHE9 shows a high degree of amino acid similarity between NHE inhibitor sensitive NHEs in the region of the NHE inhibitor recognition site that has been defined for NHE1. Second, highly significant, positive associations among drugs approved by the US Food and Drug Administration for the treatment of ADHD and drugs known to inhibit sodium hydrogen exchange were found. Positive associations between ADHD drugs and the control NSAID drugs were not found.

The high correlations among ADHD drugs validate the idea that the DRAR-CPI database can recover meaningful associations among drugs based on their predicted binding affinities with many different proteins. This result is particularly impressive given that the database does not include the primary targets of these medications (i.e. the dopamine transporter for methylphenidate and amphetamine, the norepinephrine transporter for atomoxetine, and the adrenergic, alpha-2A, receptor for guanfacine and clonidine), which are believed to mediate their therapeutic effects on ADHD.

Many significant, positive correlations were found between ADHD drugs and NHE inhibitors. In contrast, no significant positive correlations between the NSAID drugs and the ADHD drugs were found. This latter finding provides some reassurance that the above methodology was not biased to find positive correlations with ADHD drugs.

It could not be determined why some NHE inhibitors cluster with ADHD drugs and others do not. The pattern observed cannot be explained by the NHE inhibition selectivity of these compounds. The pattern of amino acid similarity among NHE proteins (FIG. 1) shows that NHE7 is more similar to NHE9 than are the other NHE proteins. Despite this similarity, the drug-protein binding profile of quinine (which selectively inhibits NHE7) was not positively correlated with any of the ADHD drugs. Comparing the above findings with the experimental NHE inhibition results reported by Masereel et al., "An Overview of Inhibitors of Na(+)/H(+) Exchanger," *Eur J Med Chem* 38:547-554 (2003), which is hereby incorporated by reference in its entirety, the NHE inhibitors that belong to the ADHD drug cluster in FIG. 2 do not show a specific pattern of NHE inhibition. Amilirode and benzamil are non-specific inhibitors, cariporide is a selective NHE1 inhibitor, and S3226 selectively inhibits NHE3. There were no positive correlations for harmaline, which selectively inhibits NHE5.

The above analysis of molecular descriptors is limited by the small sample size, which makes it difficult to show statistical significance. Nonetheless, these results offer additional validation for the idea that the use of drug-protein binding profiles to cluster drugs is sensitive to variability in molecular features. It also provides some insights into why some NHE inhibitors are associated with ADHD drugs and others are not.

Although promising, the above results are not entirely supportive of applicant's hypothesis. Notably, clonidine, is approved for the treatment of ADHD and is a modest NHE inhibitor. However, it did not cluster with the other ADHD drugs in the analysis of drug-protein binding. This finding tempers the conclusion that NHE inhibitors inhibit NHE9. Another obstacle to NHE9 inhibition is that, unlike NHEs that are currently targeted by these drugs, NHE9 is an intracellular protein, which could complicate drug delivery.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of treating attention deficit hyperactivity disorder in a subject, said method comprising:
   selecting a subject with attention deficit hyperactivity disorder and
   administering to the selected subject a sodium/hydrogen exchanger inhibitor under conditions effective to treat the selected subject for attention deficit hyperactivity disorder, wherein the sodium/hydrogen exchange inhibitor is selected from a group consisting of cariporide, amiloride, s3226, and benzamil.

2. The method of claim 1, wherein the selected subject is a human.

3. The method of claim 1, wherein said administering is carried out parenterally, orally, subcutaneously, intravenously, intramuscularly, extraperitoneally, by intranasal instillation, by inhalation, or by application to mucous membranes.

4. The method of claim 1, wherein the sodium/hydrogen exchanger inhibitor is administered in combination with a pharmaceutical carrier or diluent.

* * * * *